United States Patent
Dorwart et al.

(10) Patent No.: US 10,301,361 B2
(45) Date of Patent: *May 28, 2019

(54) α-HEMOLYSIN VARIANTS WITH ALTERED CHARACTERISTICS

(71) Applicant: Genia Technologies, Inc., Santa Clara, CA (US)

(72) Inventors: Michael Dorwart, Mountain View, CA (US); Daniel Korenblum, San Francisco, CA (US)

(73) Assignee: GENIA TECHNOLOGIES, INC., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/924,861

(22) Filed: Oct. 28, 2015

(65) Prior Publication Data

US 2017/0088588 A1    Mar. 30, 2017

Related U.S. Application Data

(60) Provisional application No. 62/073,936, filed on Oct. 31, 2014.

(51) Int. Cl.
*C07K 14/31* (2006.01)
*C12Q 1/6869* (2018.01)

(52) U.S. Cl.
CPC .......... *C07K 14/31* (2013.01); *C12Q 1/6869* (2013.01)

(58) Field of Classification Search
CPC ........ C12N 9/88; C12N 15/13; A61K 39/395; A61P 31/04; C07K 16/12; C07K 14/31; C12Q 1/68

USPC .......... 435/320.1, 340; 530/388.4; 536/23.53
See application file for complete search history.

(56) References Cited

U.S. PATENT DOCUMENTS

| | | | |
|---|---|---|---|
| 2011/0177498 A1 | 7/2011 | Clarke et al. | |
| 2011/0311965 A1* | 12/2011 | Maglia | C07K 14/245 435/6.1 |
| 2014/0134616 A1 | 5/2014 | Davis et al. | |

FOREIGN PATENT DOCUMENTS

| | | | |
|---|---|---|---|
| WO | 2010055307 A1 | 5/2010 | |
| WO | 2012164270 | 12/2012 | |
| WO | WO 2013/123450 | 8/2013 | |
| WO | WO 2014/074727 | 5/2014 | |
| WO | WO-2014100481 A2 * | 6/2014 | ............. C07K 14/31 |
| WO | PCT/US14/61853 | 10/2014 | |

OTHER PUBLICATIONS

Aksimentiev and Schulten, Imaging a-Hemolysin with Molecular Dynamics: Ionic Conductance, Osmotic Permeability, and the Electrostatic Potential Map, Biophysical Journal (2005) 88: 3745-3761.
Butler et al., Single-molecule DNA detection with an engineered MspA protein nanopore, PNAS (2008) 105(52): 20647-20652.

(Continued)

*Primary Examiner* — Jana A Hines
(74) *Attorney, Agent, or Firm* — FisherBroyles, LLP; Victoria L. Boyd; Jason M. Pass

(57) ABSTRACT

Described herein are variants of alpha-hemolysin having at least one mutation selected from T12R, T12K, N17R, N17K or combinations of T12 and N17 mutations. The variants in some embodiments may further comprise H144A. The α-hemolysin variants have a decreased time to thread.

13 Claims, 5 Drawing Sheets

Specification includes a Sequence Listing.

(56) References Cited

OTHER PUBLICATIONS

Korchev et al., Low Conductance States of a Single Ion Channel are not 'Closed', J. Membrane Biol. (1995) 147:233-239.

Krasilnikov and Sabirov, Ion Transport Through Channels Formed in Lipid Bilayers by *Staphylococcus aureus* Alpha-Toxin, Gen. Physiol. Biophys. (1989) 8:213-222.

Nakane et al., A Nanosensor for Transmembrane Capture and Identification of Single Nucleic Acid Molecules, Biophys. J. (2004) 87:615-621.

Rhee and Burns, Nanopore sequencing technology: nanopore preparations, Trends in Biotech. (2007) 25 (4):174-181.

Song et al., Structure of *Staphylococcal* α-Hemolysin, a Heptameric Transmembrane Pore, Science (1996) 274:1859-1866.

Kasianowicz et al., Characterization of individual polynucleotide molecules using a membrane channel, Proc. Natl. Acad. Sci. USA (1996) 93:13770-13773.

Akeson et al., Microsecond timescale discrimination among polycytidylic acid, polyadenylic acid, and polyuridylic acid as homopolymers or as segments within single RNA molecules, Biophys. J. (1999) 77:3227-3233.

Meller et al., Voltage-driven DNA translocations through a nanopore, Phys. Rev. Lett., 86 (2001), pp. 3435-3438.

Howorka et al., Sequence-specific detection of individual DNA strands using engineered nanopores, Nat. Biotechnol., 19 (2001a), pp. 636-639.

Howorka et al., Kinetics of duplex formation for individual DNA strands within a single protein nanopore, Proc. Natl. Acad. Sci. USA, 98 (2001b), pp. 12996-13001.

Movileanu et al., Detecting protein analytes that modulate transmembrane movement of a polymer chain within a single protein pore, Nat. Biotechnol., 18 (2000), pp. 1091-1095.

Kasianowicz et al., Nanometer-scale pores: potential applications for analyte detection and DNA characterization, Disease Markers 18 (2002), pp. 185-191.

Bond, P.J. et al., Molecular Dynamics Simulations of DNA within a Nanopore: Arginine-Phosphate Tethering and a Binding/Sliding Mechanism for Translocation, Biochemistry, (2011), pp. 3777-3783, vol. 50 No. 18.

Krasilnikov et al, 1989, "Ion Transport Through Channels Formed in Lipid Bilayers by *Staphylococcus aureus* Alpha-Toxin", General Physiology and Biophysics, 8:213-222.

Winters-Hilt, 2007, "The a-Hemolysin nanopore transduction detector—single-molecule binding studies and immunological screening of antibodies and aptamers", BMC Bioinformatics, 8(Suppl 7):S9.

Yadav et al, 2014, "Next Generation Sequencing: Potential and Application in Drug Discovery", The Scientific World Journal, vol. 2014, Article ID 802437, 7 pages.

Yegnasubramanian, Srinivasan, 2013, "Explanatory Chapter: Next Generation Sequencing [Author Manuscript]", published in final form at Methods in Enzymology, 529:201-208.

\* cited by examiner

α-HEMOLYSIN VARIANTS WITH ALTERED CHARACTERISTICS

CROSS-REFERENCE TO RELATED APPLICATIONS

The present application claims priority to U.S. Provisional Patent Application Ser. No. 62/073,936, entitled "alpha-Hemolysin Variants", filed 31 Oct. 2014.

SEQUENCE LISTING

A sequence listing comprising SEQ ID NOS: 1-8 is attached hereto. Each sequence provided in the sequence listing is incorporated herein by reference, in its entirety, for all purposes. Said ASCII copy, created on Oct. 26, 2015, is named 20-04338.P519US1_SL.txt and is 20,325 bytes in size.

TECHNICAL FIELD

Disclosed are compositions and methods relating to *Staphylococcal aureaus* alpha-hemolysin variants. The alpha-hemolysin (α-HL) variants are useful, for example, as a nanopore in a device for determining polymer sequence information. The nanopores, methods and systems described herein provide quantitative detection of single strand nucleic acids, such as DNA, RNA, etc., employing nanopore-based single-molecule technology with improved characteristics.

BACKGROUND

Hemolysins are members of a family of protein toxins that are produced by a wide variety of organisms. Some hemolysins, for example alpha hemolysins, can disrupt the integrity of a cell membrane (e.g., a host cell membrane) by forming a pore or channel in the membrane. Pores or channels that are formed in a membrane by pore forming proteins can be used to transport certain polymers (e.g., polypeptides or polynucleotides) from one side of a membrane to the other.

Alpha-hemolysin (α-HL, a-HL or alpha-HL) is a self-assembling toxin which forms an aqueous channel in the membrane of a host cell. Alpha-HL has become a principal component for the nanopore sequencing community. It has many advantageous properties including high stability, self assembly and a pore diameter which is wide enough to accommodate single stranded DNA but not double stranded DNA (Kasianowicz et al., 1996).

Previous work on DNA detection in the a-HL pore has focused on analyzing the ionic current signature as DNA translocates through the pore (Kasianowicz et al., 1996, Akeson et al., 1999, Meller et al., 2001), a very difficult task given the translocation rate (~1 nt/μs at 100 mV) and the inherent noise in the ionic current signal. Higher specificity has been achieved in nanopore-based sensors by incorporation of probe molecules permanently tethered to the interior of the pore (Howorka et al., 2001a and Howorka et al., 2001b; Movileanu et al., 2000).

The wild-type a-HL results in significant number of deletion errors, i.e. bases are not measured. Therefore, α-HL nanopores with improved properties are desired.

BRIEF SUMMARY OF THE INVENTION

The invention features a mutant staphylcoccal alpha hemolysin (αHL) polypeptide containing an amino acid variation that enhances the time to thread, e.g., decreases the time to capture of the molecule of interest.

The presently disclosed variants reduce the time thread of the molecule of interest, e.g., various tagged nucleotides or a nucleotide to be sequenced.

Disclosed herein are α-hemolysin (αHL) variants. The α-hemolysin (αHL) variants are derived from a parental α-HL polypeptide or a sequence having at least 80%, 90%, 95%, 98%, or more sequence identity to SEQ ID NO: 8, and comprises a substitution at a position corresponding to position 12 or 17 of SEQ ID NO:3 (mature a-HL). In some embodiments, the variant further comprises H144A. In some embodiments, the substitution comprises one or more positive charges. In some embodiments, the variant comprises a substitution at a position corresponding to one or more of residues T12 and/or N17. In some embodiments, the variant comprises a substitution selected from T12K, T12R, N17K, N17R and combinations thereof. In some embodiments, the variant has an altered time to thread (TTT) relative to the parent α-hemolysin. In some embodiments, the TTT is decreased. In some embodiments, the variant comprises a substitution at a position corresponding to a residue selected from the group consisting of T12R or K, and/or N17R or K in α-hemolysin (αHL) from *Staphylococcus aureus* (SEQ ID NO: 1). In some embodiments, the substitution is T12K. In some embodiments, the substitution is T12R. In some embodiments, the substitution is N17K. In some embodiments, the substitution is N17R. In some embodiments, the variant a-HL having an altered characteristic as compared to a parental α-hemolysin (e.g., AAA26598) comprises H144A and at least one additional mutation selected from a. T12K/R;
b. N17K/R;

or combinations thereof.

In all embodiments, the alpha-hemolysin has a sequence having at least 90%, preferably 95%, 98%, or more sequence identity to SEQ ID NO: 8.

In some embodiments, the amino acid substitution allows the addition of heterologous molecules, e.g., PEG. In some embodiment, the a-HL variant has post-translational modifications.

In some embodiments, the substitution is a non-native amino acid that is basic or positively charged at a pH from about 5 to about 8.5.

In some instances, a polymerase is associated with the nanopore (e.g., covalently linked to the nanopore) and the polymerase performs nucleotide incorporation events.

In an aspect, there is provided a heptomeric pore assembly comprising at least one α-hemolysin (αHL) variant as described herein. In one embodiment the invention provides a heteromeric pore assembly containing a mutant αHL polypeptide (M), e.g., a pore assembly which contains a wild type (WT) *staphylococcal* αHL polypeptide and a mutant αHL polypeptide in which an amino acid variant (as provided for herein) of the mutant αHL polypeptide occupies a position in a transmembrane channel of the pore structure. For example, the ratio of WT and variant αHL polypeptides is expressed by the formula $WT_{7-n}M_n$, where n is 1, 2, 3, 4, 5, 6, or 7; preferably the ratio of αHL polypeptides in the heteroheptamer is $WT_{7-n}M_n$; most preferably, the ratio is $WT_6M_1$. Homomeric pores in which each subunit of the heptamer is a mutated αHL polypeptide (i.e., where n=7) are also encompassed by the invention.

In an aspect, there is provided a nucleic acid encoding an a-HL variant as described herein.

In an aspect, there is provided a vector comprising a nucleic acid encoding an alpha-hemolysin variant as described herein.

In an aspect, there is provided a host cell transformed with the vector comprising a nucleic acid encoding an alpha-hemolysin variant as described herein.

In an aspect, there is provided a method of producing an alpha-hemolysin variant comprising the steps of: (a) culturing a host cell comprising a nucleic acid encoding a alpha-hemolysin variant as described herein in a suitable culture medium under suitable conditions to produce alpha-hemolysin variant; and (b) obtaining said produced alpha-hemolysin variant.

In an aspect, there is provided a method for detecting a target molecule, comprising: (a) providing a chip comprising a nanopore as described herein in a membrane that is disposed adjacent or in proximity to a sensing electrode; (b) directing a nucleic acid molecule through said nanopore, wherein said nucleic acid molecule is associated with a reporter molecule, wherein said nucleic acid molecule comprises an address region and a probe region, wherein said reporter molecule is associated with said nucleic acid molecule at said probe region, and wherein said reporter molecule is coupled to a target molecule; (c) sequencing said address region while said nucleic acid molecule is directed through said nanopore to determine a nucleic acid sequence of said address region; and (d) identifying, with the aid of a computer processor, said target molecule based upon a nucleic acid sequence of said address region determined in (c).

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIGS. 1-5 each comprise two figures, e.g., FIGS. 1A and 1B. The A figure for each figure is a histogram of the number of capture events which had a "time-to-thread" equal to the time bin shown on the x-axis. The B figure for each figure is a portion of the raw data for the corresponding figure A.

FIG. 1A (top panel) shows "time-to-thread" data. This data is combined from many pores which were capturing the tagged nucleotides indicating the pore had both a polymerase and a template DNA molecule. The mean and median values, along with the standard deviation for wild type aHL are 20.7 ms, 16.1 ms and 1.5 ms respectively, and the total number of squarewaves used for the calculations is 41910.

FIG. 1B (bottom panel) shows some raw data with five consecutive squarewaves shown. The data points between the green lines represent the open channel (where no tagged nucleotide is threaded in the pore) and the data in-between the red lines represents when the tagged nucleotide has threaded into the pore and is blocking ions moving through the channel. The electrode is cycled between positive and negative 100 mV, and in our system data points are not recorded when a negative voltage is applied. Thus, all the data points are collected from the positively applied potential, and the time where there is an absence of data points (between 1716.9-1717 sec for example) is when the electrodes have a negative voltage applied to them. In this example the "time-to-thread" measurement is calculated from squarewaves which have a threaded level observable, and, the previous squarewave had a threaded level at the end of the positive voltage (indicating that the tag was threaded in the pore and bound by the polymerase).

FIG. 2A (top panel) is data combined from many pores which were capturing the tagged nucleotides indicating the pore had both a polymerase and a template DNA molecule. The mean and median values, along with the standard deviation for T12K aHL are 19.7 ms, 14.5 ms and 1.5 ms respectively, and the total number of squarewaves used for the calculations is 4311.

FIG. 2B (bottom panel) shows some raw data with five consecutive squarewaves shown. The data points between the green lines represent the open channel (where no tagged nucleotide is threaded in the pore) and the data in-between the red lines represents when the tagged nucleotide has threaded into the pore and is blocking ions moving through the channel. The electrode is cycled between positive and negative 100 mV, and in our system data points are not recorded when a negative voltage is applied. Thus, all the data points are collected from the positively applied potential, and the time where there is an absence of data points (between 1600.4-1601.2 sec for example) is when the electrodes have a negative voltage applied to them. In this example the "time-to-thread" measurement is calculated from squarewaves which have a threaded level observable, and, the previous squarewave had a threaded level at the end of the positive voltage (indicating that the tag was threaded in the pore and bound by the polymerase).

FIG. 3A is data combined from many pores which were capturing the tagged nucleotides indicating the pore had both a polymerase and a template DNA molecule. The mean and median values, along with the standard deviation for T12R aHL are 16.9 ms, 10.5 ms and 1.5 ms respectively, and the total number of squarewaves used for the calculations is 4138.

FIG. 3B (bottom panel) shows some raw data with five consecutive squarewaves shown. The data points between the green lines represent the open channel (where no tagged nucleotide is threaded in the pore) and the data in-between the red lines represents when the tagged nucleotide has threaded into the pore and is blocking ions moving through the channel. The electrode is cycled between positive and negative 100 mV, and in our system data points are not recorded when a negative voltage is applied. Thus, all the data points are collected from the positively applied potential, and the time where there is an absence of data points (between 267.2-268.2 sec for example) is when the electrodes have a negative voltage applied to them. In this example the "time-to-thread" measurement is calculated from squarewaves which have a threaded level observable, and, the previous squarewave had a threaded level at the end of the positive voltage (indicating that the tag was threaded in the pore and bound by the polymerase).

FIG. 4A (top panel) is data combined from many pores which were capturing the tagged nucleotides indicating the pore had both a polymerase and a template DNA molecule. The mean and median values, along with the standard deviation for N17R aHL are 17.5 ms, 10.5 ms and 1.7 ms respectively, and the total number of squarewaves used for the calculations is 3877.

FIG. 4B (bottom panel) shows some raw data with five consecutive squarewaves shown. The data points between the green lines represent the open channel (where no tagged nucleotide is threaded in the pore) and the data in-between the red lines represents when the tagged nucleotide has threaded into the pore and is blocking ions moving through the channel. The electrode is cycled between positive and negative 100 mV, and in our system data points are not recorded when a negative voltage is applied. Thus, all the data points are collected from the positively applied potential, and the time where there is an absence of data points (between 344-344.9 sec for example) is when the electrodes have a negative voltage applied to them. In this example the "time-to-thread" measurement is calculated from squarewaves which have a threaded level observable, and, the previous squarewave had a threaded level at the end of the positive voltage (indicating that the tag was threaded in the pore and bound by the polymerase).

FIG. 5A (top panel) shows combined data from many pores which were capturing the tagged nucleotides indicating the pore had both a polymerase and a template DNA molecule. The mean and median values, along with the standard deviation for N17K aHL are 5.7 ms, 2.4 ms and 0.7 ms respectively, and the total number of squarewaves used for the calculations is 2424.

FIG. 5B (bottom panel) shows some raw data with five consecutive squarewaves shown. The data points between the green lines represent the open channel (where no tagged nucleotide is threaded in the pore) and the data in-between the red lines represents when the tagged nucleotide has threaded into the pore and is blocking ions moving through the channel. The electrode is cycled between positive and negative 100 mV, and in our system data points are not recorded when a negative voltage is applied. Thus, all the data points are collected from the positively applied potential, and the time where there is an absence of data points (between 79.5-80.5 sec for example) is when the electrodes have a negative voltage applied to them. In this example the "time-to-thread" measurement is calculated from squarewaves which have a threaded level observable, and, the previous squarewave had a threaded level at the end of the positive voltage (indicating that the tag was threaded in the pore and bound by the polymerase).

DETAILED DESCRIPTION

Figure 1A:
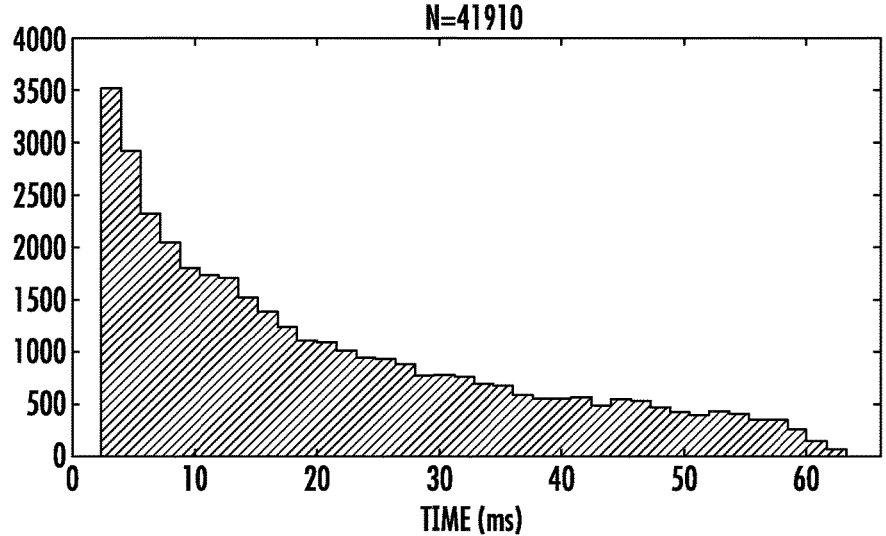
FIGS. 1A and 1B show the results for the wild-type a-hemolysin nanopore.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range. The term about is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Definitions

Alpha-hemolysin: As used herein, "alpha-hemolysin," "α-hemolysin," "a-HL" and "α-HL" are used interchangeably and refer to the monomeric protein that self-assembles into a heptameric water-filled transmembrane channel (i.e., nanopore). Depending on context, the term may also refer to the transmembrane channel formed by seven monomeric proteins.

Amino acid: As used herein, the term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" or "non-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

Base Pair (bp): As used herein, base pair refers to a partnership of adenine (A) with thymine (T), or of cytosine (C) with guanine (G) in a double stranded DNA molecule.

Complementary: As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

Expression cassette: An "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

Heterologous: A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

Host cell: By the term "host cell" is meant a cell that contains a vector and supports the replication, and/or transcription or transcription and translation (expression) of the expression construct. Host cells for use in the present invention can be prokaryotic cells, such as *E. coli* or *Bacillus subtilus*, or eukaryotic cells such as yeast, plant, insect, amphibian, or mammalian cells. In general, host cells are prokaryotic, e.g., *E. coli*.

Isolated: An "isolated" molecule is a nucleic acid molecule that is separated from at least one other molecule with which it is ordinarily associated, for example, in its natural environment. An isolated nucleic acid molecule includes a nucleic acid molecule contained in cells that ordinarily express the nucleic acid molecule, but the nucleic acid molecule is present extrachromasomally or at a chromosomal location that is different from its natural chromosomal location.

Modified alpha-hemolysin: As used herein, the term "modified alpha-hemolysin" refers to an alpha-hemolysin originated from another (i.e., parental) alpha-hemolysin and contains one or more amino acid alterations (e.g., amino acid substitution, deletion, or insertion) compared to the parental alpha-hemolysin. In some embodiments, a modified alpha-hemolysin of the invention is originated or modified from a naturally-occurring or wild-type alpha-hemolysin. In some embodiments, a modified alpha-hemolysin of the invention is originated or modified from a recombinant or engineered alpha-hemolysin including, but not limited to, chimeric alpha-hemolysin, fusion alpha-hemolysin or another modified alpha-hemolysin. Typically, a modified alpha-hemolysin has at least one changed phenotype compared to the parental alpha-hemolysin.

Mutation: As used herein, the term "mutation" refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence.

Nanopore: The term "nanopore," as used herein, generally refers to a pore, channel or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha-hemolysin is an example of a protein nanopore.

Nucleic Acid Molecule: The term "nucleic acid molecule" includes RNA, DNA and cDNA molecules. It will be understood that, as a result of the degeneracy of the genetic code, a multitude of nucleotide sequences encoding a given protein such as alpha-hemolysin and/or variants thereof may be produced. The present invention contemplates every possible variant nucleotide sequence, encoding variant alpha-hemolysin, all of which are possible given the degeneracy of the genetic code.

Promoter: As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

Purified: As used herein, "purified" means that a molecule is present in a sample at a concentration of at least 95% by weight, or at least 98% by weight of the sample in which it is contained.

Purifying: As used herein, the term "purifying" generally refers to subjecting transgenic nucleic acid or protein containing cells to biochemical purification and/or column chromatography.

Tag: As used herein, the term "tag" refers to a detectable moiety that may be atoms or molecules, or a collection of atoms or molecules. A tag may provide an optical, electrochemical, magnetic, or electrostatic (e.g., inductive, capacitive) signature, which signature may be detected with the aid of a nanopore. Typically, when a nucleotide is attached to the tag it is called a "Tagged Nucleotide." The tag may be attached to the nucleotide via the phosphate moiety.

Time-To-Thread: The term "time to thread" or "TTT" means the time it takes the polymerase-tag complex or a nucleic add strand to thread the tag into the barrel of the nanopore.

Variant: As used herein, the term "variant" refers to a modified protein which displays altered characteristics when compared to the parental protein, e.g., altered ionic conductance.

Variant hemolysin: The term "variant hemolysin gene" or "variant hemolysin" means, respectively, that the nucleic acid sequence of the alpha-hemolysin gene from *Staphylococcus aureus* has been altered by removing, adding, and/or manipulating the coding sequence or the amino acid sequence of the expressed protein has been modified consistent with the invention described herein.

Vector: As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Wild-type: As used herein, the term "wild-type" refers to a gene or gene product which has the characteristics of that gene or gene product when isolated from a naturally-occurring source.

Percent homology: The term "% homology" is used interchangeably herein with the term "% identity" herein and refers to the level of nucleic acid or amino acid sequence identity between the nucleic acid sequence that encodes any one of the inventive polypeptides or the inventive polypeptide's amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for any one of the inventive polypeptides, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, S. F., et al., Nucleic Acids Res. 25:3389-3402, 1997.)

A preferred alignment of selected sequences in order to determine "% identity" between two or more sequences, is performed using for example, the CLUSTAL-W program in MacVector version 13.0.7, operated with default parameters, including an open gap penalty of 10.0, an extended gap penalty of 0.1, and a BLOSUM 30 similarity matrix.

Nomenclature

In the present description and claims, the conventional one-letter and three-letter codes for amino acid residues are used.

For ease of reference, variants of the application are described by use of the following nomenclature:

Original amino acid(s): position(s): substituted amino acid(s). According to this nomenclature, for instance the substitution of threonine by an arginine in position 17 is shown as:

Thr17Arg or T17R

Multiple mutations are separated by plus signs, i.e.:

Thr17Arg+Glu34Ser or T17R+E34S representing mutations in positions 30 and 34 substituting alanine and glutamic acid for asparagine and serine, respectively.

When one or more alternative amino acid residues may be inserted in a given position it is indicated as: T17R/K, or T17R or T17K.

Site-Directed Mutagenesis of Alpha-Hemolysin

*Staphylococcus aureus* alpha hemolysin wild type sequences are provided herein (SEQ ID NO:1, nucleic acid coding region; SEQ ID NO:3, protein coding region) and available elsewhere (National Center for Bioinformatics or GenBank Accession Numbers M90536 and AAA26598).

Point mutations may be introduced using QuikChange Lightning 2 kit (Stategene/Agilent) following manufacturer's instructions.

Primers can be ordered from commercial companies, e.g., IDT DNA.

Nanopore Assembly and Insertion

The methods described herein can use a nanopore having a polymerase attached to the nanopore. In some cases, it is desirable to have one and only one polymerase per nanopore (e.g., so that only one nucleic acid molecule is sequenced at each nanopore). However, many nanopores, including alpha-hemolysin (aHL), can be multimeric proteins having a plurality of subunits (e.g., 7 subunits for aHL). The subunits can be identical copies of the same polypeptide. Provided herein are multimeric proteins (e.g., nanopores) having a defined ratio of modified subunits (e.g., a-HL variants) to un-modified subunits (e.g., a-HL). Also provided herein are methods for producing multimeric proteins (e.g., nanopores) having a defined ratio of modified subunits to un-modified subunits.

With reference to FIG. 27 of WO2014/074727, a method for assembling a protein having a plurality of subunits comprises providing a plurality of first subunits 2705 and providing a plurality of second subunits 2710, where the second subunits are modified when compared with the first subunits. In some cases, the first subunits are wild-type (e.g., purified from native sources or produced recombinantly). The second subunits can be modified in any suitable way. In some cases, the second subunits have a protein (e.g., a polymerase) attached (e.g., as a fusion protein).

The modified subunits can comprise a chemically reactive moiety (e.g., an azide or an alkyne group suitable for forming a linkage). In some cases, the method further comprises performing a reaction (e.g., a Click chemistry cycloaddition) to attach an entity (e.g., a polymerase) to the chemically reactive moiety.

The method can further comprise contacting the first subunits with the second subunits 2715 in a first ratio to form a plurality of proteins 2720 having the first subunits and the second subunits. For example, one part modified aHL subunits having a reactive group suitable for attaching a polymerase can be mixed with six parts wild-type aHL subunits (i.e., with the first ratio being 1:6). The plurality of proteins can have a plurality of ratios of the first subunits to the second subunits. For example, the mixed subunits can form several nanopores having a distribution of stoichiometries of modified to un-modified subunits (e.g., 1:6, 2:5, 3:4).

In some cases, the proteins are formed by simply mixing the subunits. In the case of aHL nanopores for example, a detergent (e.g., deoxycholic acid) can trigger the aHL monomer to adopt the pore conformation. The nanopores can also be formed using a lipid (e.g., 1,2-diphytanoyl-sn-glycero-3-phosphocholine (DPhPC) or 1,2-di-0-phytanyl-sn-glycero-3-phosphocholine (DoPhPC)) and moderate temperature (e.g., less than about 100° C.). In some cases, mixing DPhPC with a buffer solution creates large multi-lamellar vesicles (LMV), and adding aHL subunits to this solution and incubating the mixture at 40° C. for 30 minutes results in pore formation.

If two different types of subunits are used (e.g., the natural wild type protein and a second aHL monomer which can contain a single point mutation), the resulting proteins can have a mixed stoichiometry (e.g., of the wild type and mutant proteins). The stoichiometry of these proteins can follow a formula which is dependent upon the ratio of the concentrations of the two proteins used in the pore forming reaction. This formula is as follows:

$$100 P_m = 100[n!/m!(n-m)!] \cdot f_{mut}^m \cdot f_{wt}^{n-m}, \text{ where}$$

$P_m$=probability of a pore having m number of mutant subunits n=total number of subunits (e.g., 7 for aHL)

m=number of "mutant" subunits $f_{mut}$=fraction or ratio of mutant subunits mixed together $f_{wt}$=fraction or ratio of wild-type subunits mixed together The method can further comprise fractionating the plurality of proteins to enrich proteins that have a second ratio of the first subunits to the second subunits 2725. For example, nanopore proteins can be isolated that have one and only one modified subunit (e.g., a second ratio of 1:6). However, any second ratio is suitable. A distribution of second ratios can also be fractionated such as enriching proteins that have either one or two modified subunits. The total number of subunits forming the protein is not always 7 (e.g., a different nanopore can be used or an alpha-hemolysin nanopore can form having six subunits) as depicted in FIG. 27 of WO2014/074727. In some cases, proteins having only one modified subunit are enriched. In such cases, the second ratio is 1 second subunit per (n−1) first subunits where n is the number of subunits comprising the protein.

The first ratio can be the same as the second ratio, however this is not required. In some cases, proteins having mutated monomers can form less efficiently than those not having mutated subunits. If this is the case, the first ratio can be greater than the second ratio (e.g., if a second ratio of 1 mutated to 6 non-mutated subunits are desired in a nanopore, forming a suitable number of 1:6 proteins may require mixing the subunits at a ratio greater than 1:6).

Proteins having different second ratios of subunits can behave differently (e.g., have different retention times) in a separation. In some cases, the proteins are fractionated using chromatography, such as ion exchange chromatography or affinity chromatography. Since the first and second subunits can be identical apart from the modification, the number of modifications on the protein can serve as a basis for separation. In some cases, either the first or second subunits have a purification tag (e.g., in addition to the modification) to allow or improve the efficiency of the fractionation. In some cases, a poly-histidine tag (His-tag), a streptavidin tag (Strep-tag), or other peptide tag is used. In some instances, the first and second subunits each comprise different tags and the fractionation step fractionates on the basis of each tag. In the case of a His-tag, a charge is created on the tag at low pH (Histidine residues become positively charged below the pKa of the side chain). With a significant difference in charge on one of the aHL molecules compared to the others, ion exchange chromatography can be used to separate the oligomers which have 0, 1, 2, 3, 4, 5, 6, or 7 of the "charge-tagged" aHL subunits. In principle, this charge tag can be a string of any amino acids which carry a uniform charge. FIG. 28 and FIG. 29 show examples of fractionation of nanopores based on a His-tag. FIG. 28 shows a plot of ultraviolet absorbance at 280 nanometers, ultraviolet absorbance at 260 nanometers, and conductivity. The peaks correspond to nanopores with various ratios of modified and unmodified subunits. FIG. 29 of WO2014/074727 shows fractionation of aHL nanopores and mutants thereof using both His-tag and Strep-tags.

In some cases, an entity (e.g., a polymerase) is attached to the protein following fractionation. The protein can be a nanopore and the entity can be a polymerase. In some instances, the method further comprises inserting the proteins having the second ratio subunits into a bilayer.

In some situations, a nanopore can comprise a plurality of subunits. A polymerase can be attached to one of the subunits and at least one and less than all of the subunits comprise a first purification tag. In some examples, the nanopore is alpha-hemolysin or a variant thereof. In some instances, all of the subunits comprise a first purification tag or a second purification tag. The first purification tag can be a poly-histidine tag (e.g., on the subunit having the polymerase attached).

Polymerase Attached to Nanopore

In some cases, a polymerase (e.g., DNA polymerase) is attached to and/or is located in proximity to the nanopore. The polymerase can be attached to the nanopore before or after the nanopore is incorporated into the membrane. In some instances, the nanopore and polymerase are a fusion protein (i.e., single polypeptide chain).

The polymerase can be attached to the nanopore in any suitable way. In some cases, the polymerase is attached to the nanopore (e.g., hemolysin) protein monomer and then the full nanopore heptamer is assembled (e.g., in a ratio of one monomer with an attached polymerase to 6 nanopore (e.g., hemolysin) monomers without an attached polymerase). The nanopore heptamer can then be inserted into the membrane.

Another method for attaching a polymerase to a nanopore involves attaching a linker molecule to a hemolysin monomer or mutating a hemolysin monomer to have an attachment site and then assembling the full nanopore heptamer (e.g., at a ratio of one monomer with linker and/or attachment site to 6 hemolysin monomers with no linker and/or attachment site). A polymerase can then be attached to the attachment site or attachment linker (e.g., in bulk, before inserting into the membrane). The polymerase can also be attached to the attachment site or attachment linker after the (e.g., heptamer) nanopore is formed in the membrane. In some cases, a plurality of nanopore-polymerase pairs are inserted into a plurality of membranes (e.g., disposed over the wells and/or electrodes) of the biochip. In some instances, the attachment of the polymerase to the nanopore complex occurs on the biochip above each electrode.

The polymerase can be attached to the nanopore with any suitable chemistry (e.g., covalent bond and/or linker). In some cases, the polymerase is attached to the nanopore with molecular staples. In some instances, molecular staples comprise three amino acid sequences (denoted linkers A, B and C). Linker A can extend from a hemolysin monomer, Linker B can extend from the polymerase, and Linker C then can bind Linkers A and B (e.g., by wrapping around both Linkers A and B) and thus the polymerase become the nanopore. Linker C can also be constructed to be part of Linker A or Linker B, thus reducing the number of linker molecules.

In some instances, the polymerase is linked to the nanopore using Solulink™ chemistry. Solulink™ can be a reaction between HyNic (6-hydrazino-nicotinic acid, an aromatic hydrazine) and 4FB (4-formylbenzoate, an aromatic aldehyde). In some instances, the polymerase is linked to the nanopore using Click chemistry (available from LifeTechnologies for example). In some cases, zinc finger mutations are introduced into the hemolysin molecule and then a molecule is used (e.g., a DNA intermediate molecule) to link the polymerase to the zinc finger sites on the hemolysin.

Apparatus Set-Up

The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide). See, for example, WO 2013/123450, for the apparatus and device set-up for sensing a nucleotide or tag.

Pore based sensors (e.g., biochips) can be used for electro-interrogation of single molecules. A pore based sensor can include a nanopore of the present disclosure formed in a membrane that is disposed adjacent or in proximity to a sensing electrode. The sensor can include a counter electrode. The membrane includes a trans side (i.e., side facing the sensing electrode) and a cis side (i.e., side facing the counter electrode).

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds).

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

Expression and Recovery

This example illustrates the expression and recovery of protein from bacterial host cells, e.g., E. coli.

DNA encoding the wild-type a-HL was purchased from a commercial source. The sequence was verified by sequencing.

Plasmid Construction.

The gene encoding either a wild-type or variant α-hemolysin was inserted into a pPR-IBA2 plasmid (IBA Life Sciences, Germany) under the control of T7 promoter.

Transformation.

E. coli BL21 DE3 (from Life Technologies) cells were transformed with the expression vector comprising the DNA encoding the wild-type or variant α-hemolysin using techniques well-known in the art. Briefly, the cells were thawed on ice (if frozen). Next, the desired DNA (in a suitable vector/plasmid) was added directly into the competent cells (should not exceed 5% of that of the competent cells) and mixed by flicking the tube. The tubes were placed on ice for 20 minutes. Next, the cells were placed in a 42° C. water bath for 45 seconds without mixing, followed by placing the tubes on ice for 2 min. The cells were then transferred to a 15 ml sterilized culture tube containing 0.9 ml of SOC medium (pre-warmed at room temperature) and cultured at 37° C. for 1 hr in a shaker. Finally, an aliquot of the cells were spread onto a LB agar plate containing the appropriate antibiotic and the plates incubated at 37° C. overnight.

Protein Expression.

Following transformation, colonies were picked and inoculated into a small volume (e.g., 3 ml) of growth medium (e.g., LB broth) containing the appropriate antibiotic with shaking at 37° C., overnight.

The next morning, transfer 1 ml of the overnight culture to a new 100 ml of autoinduction medium, e.g., Magic Media (Life Technologies) containing an appropriate antibiotic to select the expression plasmid. Grow the culture with shaking at 25° C. approximately 16 hrs but this depended on the expression plasmids. Cells were harvested by centrifugation at 3,000 g for 20 min at 4° C. and stored at −80° C. until used.

Purification.

Cells were lysed via sonication. The alpha-hemolysin was purified to homogeneity by affinity column chromatography.

Example 2

T12 and/or N17 Variants

The following example details the introduction of a mutation at a desired residue.

Mutations.

Site-directed mutagenesis is carried out using a QuikChange Multi Site-Directed Mutagenesis kit (Stratagene, La Jolla, Calif.) to prepare the T12 and/or N17 variants.

The variants were expressed and purified as in Example 1.

Example 3

Assembly of Nanopore

This example describes the assembly of a nanopore comprising six a-HL variant subunits and one wild-type subunit.

The wild-type a-HL was expressed as described in Example 1 with SpyTag and a HisTag and purified on a cobalt affinity column using a cobalt elution buffer (200 mM NaCl, 300 mM imidazole, 50 mM tris, pH 8). The desired a-HL variant was expressed as described in Example 1 with a StrepTag and purified using a Streptactin affinity column on the fast protein liquid chromatography (FPLC) using an elution buffer (50 mM tris, 5 mM desthiobiotin, 200 mM NaCl, pH 8). The proteins were stored at 4° C. if used within 5 days, otherwise 8% trehalose was added and stored at −80° C.

Using approximately 20 mg of total protein, the wild-type a-HL to desired a-HL variant solutions were mixed together at the 1:6 ratio. Diphytanoylphosphatidylcholine (DPhPC) lipid was solubilized in either 50 mM Tris, 200 mM NaCl, pH 8 or 150 mM KCl, 30 mM HEPES, pH 7.5 to a final concentration of 50 mg/ml and added to the mixture of a-HL monomers to a final concentration of 5 mg/ml. The mixture of the a-HL monomers was incubated at 40° C. for at least 10 min. The lipid hemolysin mixture is applied to a size-exclusion chromatography column to separate the lipid from the oligomerized proteins.

Example 4

Attachment of a Polymerase

This example provides for the attachment of a polymerase to a nanopore.

The polymerase may be coupled to the nanopore by any suitable means. See, for example, PCT/US2013/068967 (published as WO2014/074727; Genia Technologies), PCT/US2005/009702 (published as WO2006/028508), and PCT/US2011/065640 (published as WO2012/083249; Columbia Univ).

The polymerase, e.g., phi29 DNA Polymerase, was coupled to a protein nanopore (e.g. alpha-hemolysin), through a linker molecule. Specifically, the SpyTag and SpyCatcher system, that spontaneously forms covalent iso-peptide linkages under physiological conditions was used. See, for example, Li et al, J Mol Biol. 2014 Jan. 23; 426(2):309-17.

The Sticky phi29 SpyCatcher HisTag was expressed according to Example 1 and purified using a cobalt affinity column. The SpyCatcher polymerase and the SpyTag oligomerized protein were incubated overnight at 4° C. in 3 mM $SrCl_2$. The 1:6-polymerase-template complex is then purified using size-exclusion chromatography.

Example 5

Activity of the Variants

This example shows the activity of the nanopores as provided by Example 3 (nanopores with an attached polymerase).

The wild-type and variant nonpores were assayed to determine the effect of a mutation at one or more positions. The assay was designed to measure the time it takes to capture a tagged molecule by a DNA polymerase attached to the nanopore using alternating voltages, i.e., squarewaves.

The bilayers were formed and pores were inserted as described in PCT/US14/61853 filed 23 Oct. 2014. The nanopore device (or sensor) used to detect a molecule (and/or sequence a nucleic acid) was set-up as described in WO2013123450.

To measure the time it takes to capture a tagged nucleotide by a DNA polymerase in our sequencing complex we have devised an assay that uses alternating positive and negative voltages (squarewaves) to determine the amount of time this takes. Our sequencing complex is comprised of a protein nanopore (αHL) which is attached to a single DNA polymerase (see Example 4). The tagged nucleotides are negatively charged, and are therefore attracted to the nanopore when the voltage applied is positive in nature, and repelled when the voltage applied to the nanopore sequencing complex is negative. So we can measure the time it takes for a tag to thread into the pore by cycling the voltage between positive and negative potentials and determine how much time the nanopore's current is unobstructed (open channel) verses when the tag is threaded (reduced current flux).

To carry out this "time-to-thread" assay the Genia Sequencing device is used with a Genia Sequencing Chip. The electrodes are conditioned and phospholipid bilayers are established on the chip as explained in PCT/US2013/026514. Genia's sequencing complex is inserted to the bilayers following the protocol described in PCT/US2013/026514 (published as WO2013/123450). The time-to-thread data shown in this patent was collected using a buffer system comprised of 20 mM HEPES pH 7.5, 300 mM KCl, 3 uM tagged nucleotide, 3 mM $Ca^{2+}$, with a voltage applied of +/−100 mV with a duty cycle of 5 Hz. After the data was collected it was analyzed for squarewaves that showed the capture of a tagged nucleotide (threaded level) which lasted to the end of the positive portion of the squarewave, and was followed by another tag capture on the subsequent squarewave. The time-to-thread was measured by determining how long the second squarewave reported unobstructed open channel current. As an example, if 10 consecutive squarewaves showed tagged nucleotide captures that lasted to the end of the positive portion of the squarewave then the time-to-thread parameter would be calculated from squarewaves 2-10 (the first squarewave does not factor into the calculation because the polymerase did not have a tag bound to it in the previous squarewave). These time-to-thread numbers were then collected for all of the pores in the experiment and statistical parameters extracted from them (such as a mean, median, standard deviation etc.).

Figure 1B:
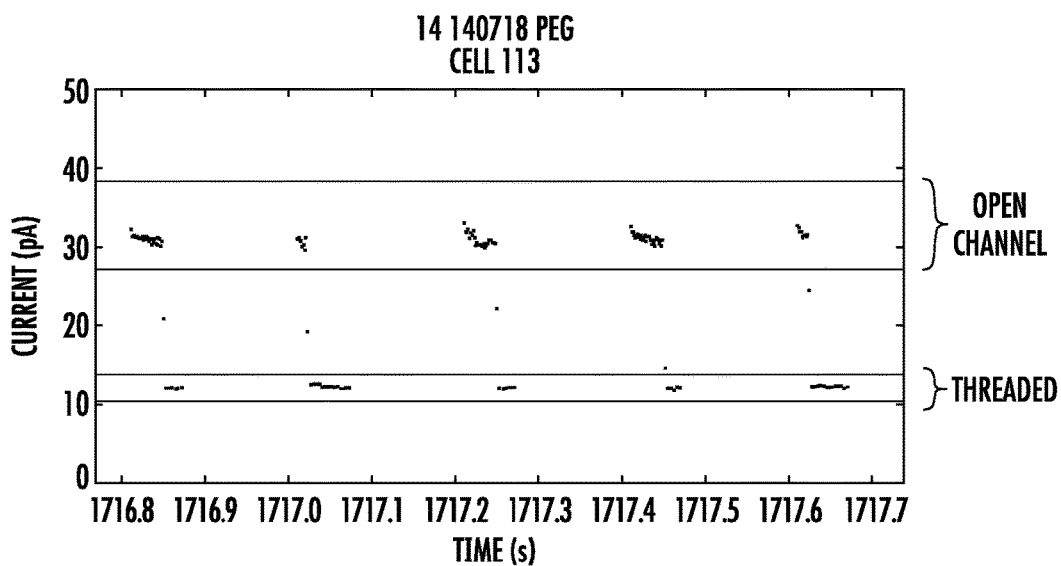
Figure 2A:
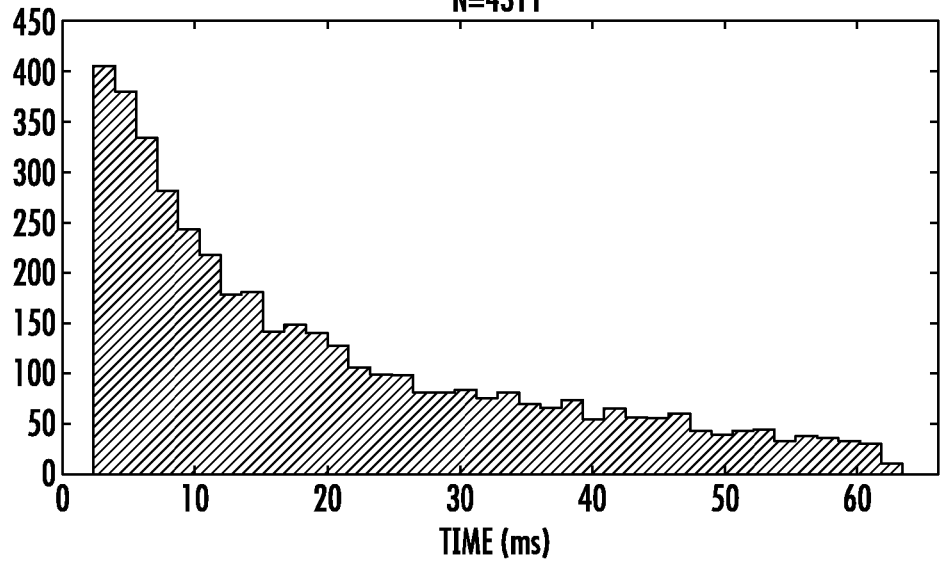
FIGS. 2A and 2B show the results for the a-hemolysin nanopore comprising a T12K mutation.
Figure 2B:
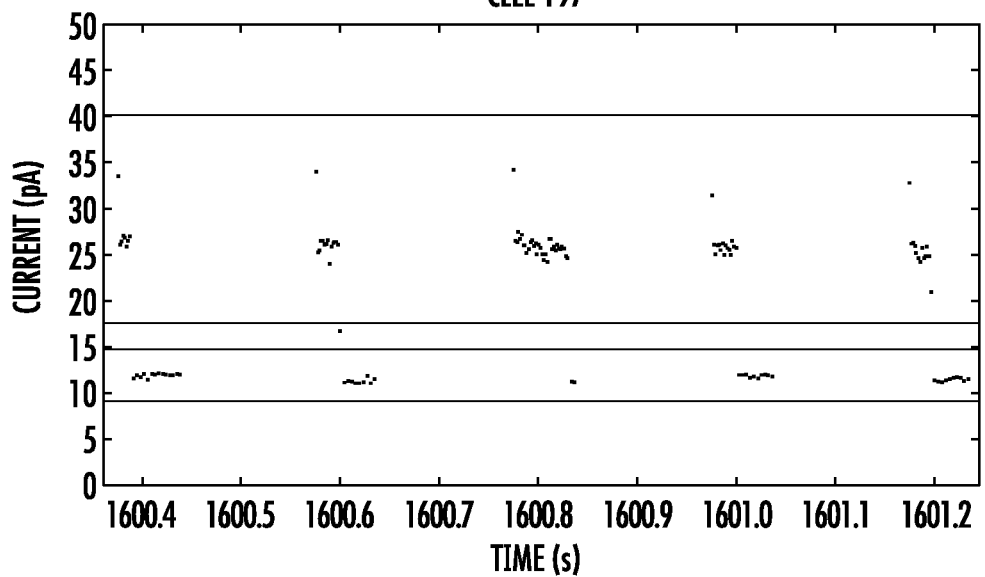
Figure 3A:
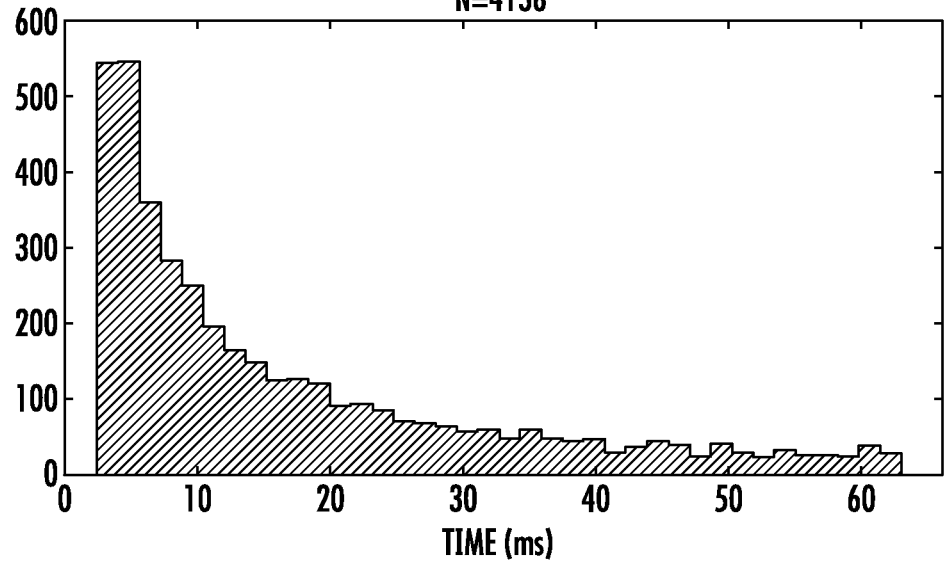
FIGS. 3A and 3B show the results for the a-hemolysin nanopore comprising a T12R mutation.
Figure 3B:
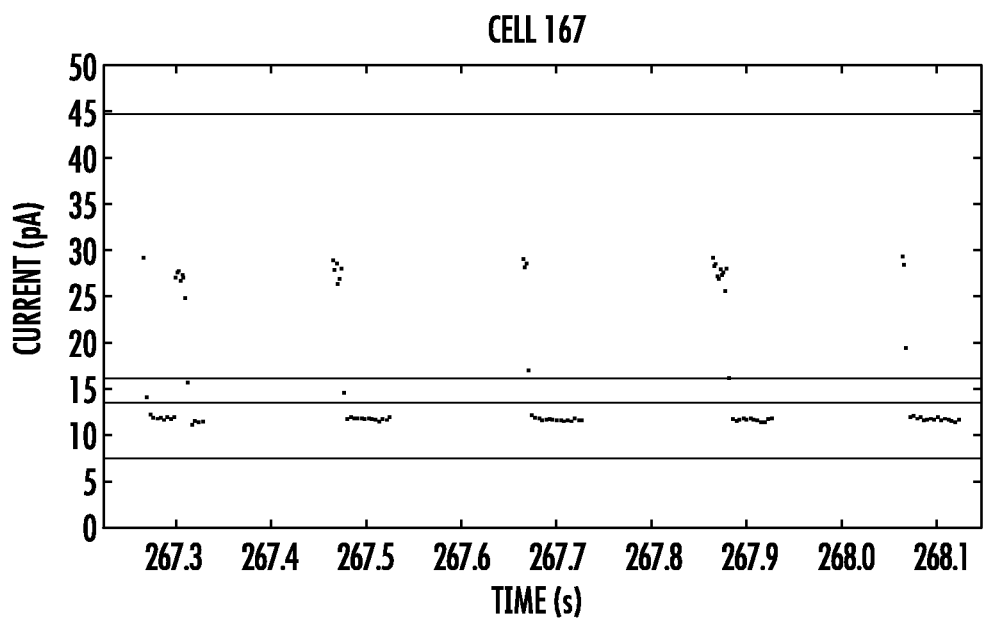
Figure 4A:
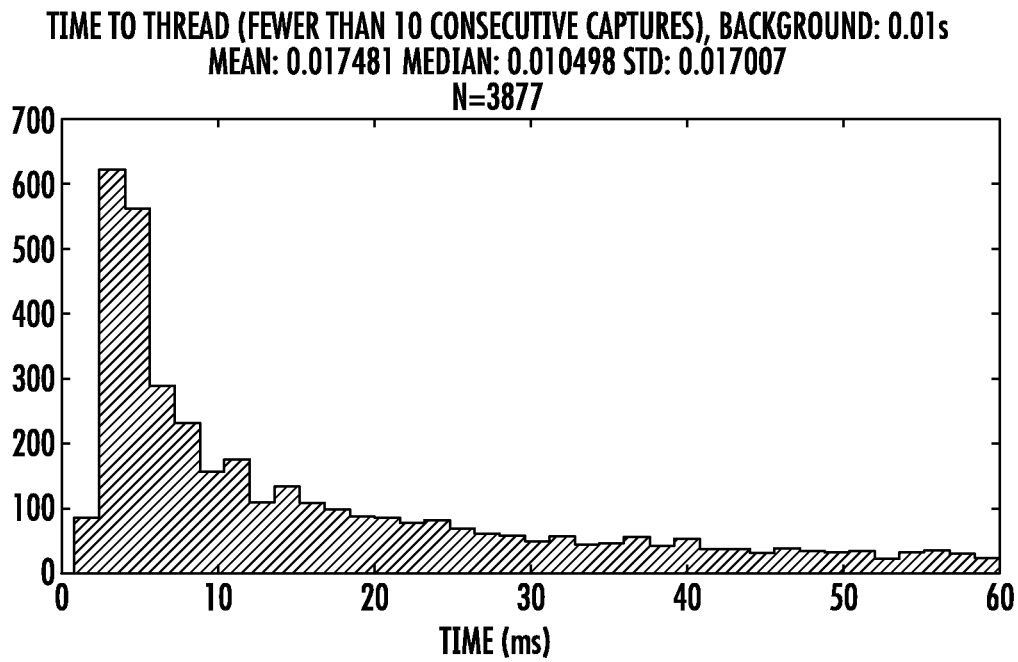
FIGS. 4A and 4B show the results for the a-hemolysin nanopore comprising a N17R mutation.
Figure 4B:
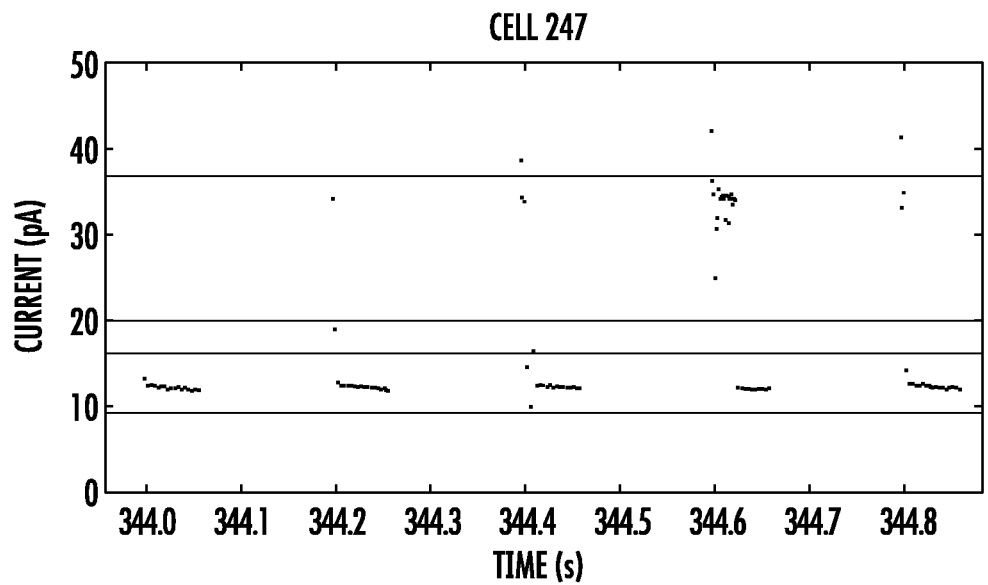
Figure 5A:
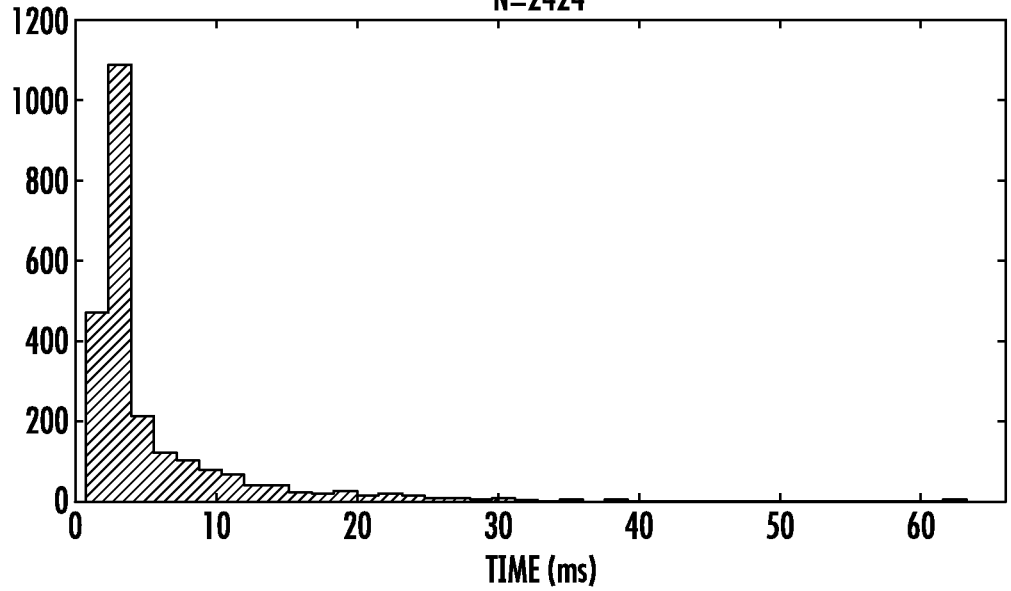
FIGS. 5A and 5B show the results for the a-hemolysin nanopore comprising a N17K mutation.
Figure 5B:
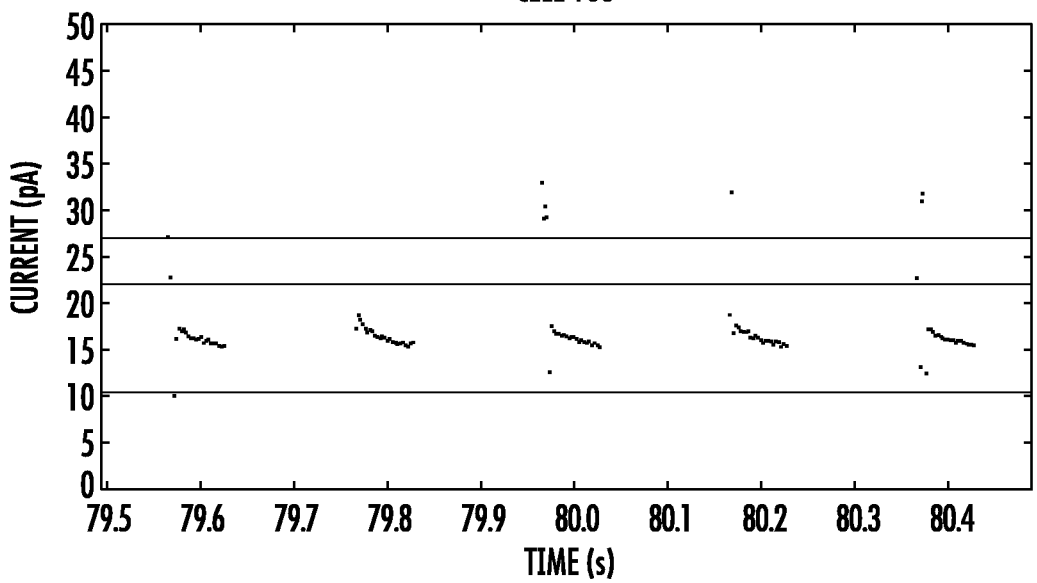

Results are shown in FIGS. 1-5.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING FREE TEXT

```
SEQ ID NO: 1 (WT aHL DNA)
ATGGCAGATC TCGATCCCGC GAAATTAATA CGACTCACTA TAGGGAGGCC    50
ACAACGGTTT CCCTCTAGAA ATAATTTTGT TTAACTTTAA GAAGGAGATA   100
TACAAATGGA TTCAGATATT AATATTAAAA CAGGTACAAC AGATATTGGT   150
TCAAATACAA CAGTAAAAAC TGGTGATTTA GTAACTTATG ATAAAGAAAA   200
TGGTATGCAT AAAAAAGTAT TTTATTCTTT TATTGATGAT AAAAATCATA   250
ATAAAAAATT GTTAGTTATT CGTACAAAAG GTACTATTGC AGGTCAATAT   300
AGAGTATATA GTGAAGAAGG TGCTAATAAA AGTGGTTTAG CATGGCCATC   350
TGCTTTTAAA GTTCAATTAC AATTACCTGA TAATGAAGTA GCACAAATTT   400
CAGATTATTA TCCACGTAAT AGTATTGATA CAAAAGAATA TATGTCAACA   450
TTAACTTATG GTTTTAATGG TAATGTAACA GGTGATGATA CTGGTAAAAT   500
TGGTGGTTTA ATTGGTGCTA ATGTTTCAAT TGGTCATACA TTAAAATATG   550
```

| SEQUENCE LISTING FREE TEXT |
| --- |

```
TACAACCAGA TTTTAAAACA ATTTTAGAAA GTCCTACTGA TAAAAAAGTT    600
GGTTGGAAAG TAATTTTTAA TAATATGGTT AATCAAAATT GGGGTCCTTA    650
TGATCGTGAT AGTTGGAATC CTGTATATGG TAATCAATTA TTTATGAAAA    700
CAAGAAATGG TTCTATGAAA GCAGCTGATA ATTTCTTAGA TCCAAATAAA    750
GCATCAAGTT TATTATCTTC AGGTTTTTCT CCTGATTTTG CAACAGTTAT    800
TACTATGGAT AGAAAAGCAT CAAAACAACA AACAAATATT GATGTTATTT    850
ATGAACGTGT AAGAGATGAT TATCAATTAC ATTGGACATC AACTAATTGG    900
AAAGGTACAA ATACTAAAGA TAAATGGACA GATAGAAGTT CAGAAAGATA    950
TAAAATTGAT TGGGAAAAAG AAGAAATGAC AAATGGTCTC AGCGCTTGGA   1000
GCCACCCGCA GTTCGAAAAA TAA                                1023

SEQ ID NO: 2 (WT aHL amino acids)[as expressed in E. coli]
MADSDINIKT GTTDIGSNTT VKTGDLVTYD KENGMHKKVF YSFIDDKNHN     50
KKLLVIRTKG TIAGQYRVYS EEGANKSGLA WPSAFKVQLQ LPDNEVAQIS    100
DYYPRNSIDT KEYMSTLTYG FNGNVTGDDT GKIGGLIGAN VSIGHTLKYV    150
QPDFKTILES PTDKKVGWKV IFNNMVNQNW GPYDRDSWNP VYGNQLFMKT    200
RNGSMKAADN FLDPNKASSL LSSGFSPDFA TVITMDRKAS KQQTNIDVIY    250
ERVRDDYQLH WTSTNWKGTN TKDKWTDRSS ERYKIDWEKE EMTNGLSAWS    300
HPQFEK                                                   306

SEQ ID NO: 3 (Mature WT aHL sequence for numbering)
ADSDINIKTG TTDIGSNTTV KTGDLVTYDK ENGMHKKVFY SFIDDKNHNK     50
KLLVIRTKGT IAGQYRVYSE EGANKSGLAW PSAFKVQLQL PDNEVAQISD    100
YYPRNSIDTK EYMSTLTYGF NGNVTGDDTG KIGGLIGANV SIGHTLKYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTNGLSAWSH    300
PQFEK                                                    305

SEQ ID NO: 4 (N17K aHL amino acids)
ADSDINIKTG TTDIGSKTTV KTGDLVTYDK ENGMHKKVFY SFIDDKNHNK     50
KLLVIRTKGT IAGQYRVYSE EGANKSGLAW PSAFKVQLQL PDNEVAQISD    100
YYPRNSIDTK EYMSTLTYGF NGNVTGDDTG KIGGLIGANV SIGHTLKYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTNGLSAWSH    300
PQFEK                                                    305

SEQ ID NO: 5 (N17R aHL amino acids)
ADSDINIKTG TTDIGSRTTV KTGDLVTYDK ENGMHKKVFY SFIDDKNHNK     50
KLLVIRTKGT IAGQYRVYSE EGANKSGLAW PSAFKVQLQL PDNEVAQISD    100
YYPRNSIDTK EYMSTLTYGF NGNVTGDDTG KIGGLIGANV SIGHTLKYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTNGLSAWSH    300
PQFEK                                                    305

SEQ ID NO: 6 (T12K aHL amino acids)
ADSDINIKTG TKDIGSNTTV KTGDLVTYDK ENGMHKKVFY SFIDDKNHNK     50
KLLVIRTKGT IAGQYRVYSE EGANKSGLAW PSAFKVQLQL PDNEVAQISD    100
YYPRNSIDTK EYMSTLTYGF NGNVTGDDTG KIGGLIGANV SIGHTLKYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTNGLSAWSH    300
PQFEK                                                    305

SEQ ID NO: 7 (T12R aHL amino acids)
ADSDINIKTG TRDIGSNTTV KTGDLVTYDK ENGMHKKVFY SFIDDKNHNK     50
KLLVIRTKGT IAGQYRVYSE EGANKSGLAW PSAFKVQLQL PDNEVAQISD    100
YYPRNSIDTK EYMSTLTYGF NGNVTGDDTG KIGGLIGANV SIGHTLKYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTNGLSAWSH    300
PQFEK                                                    305

SEQ ID NO: 8 (Mature WT aHL; AAA26598)
ADSDINIKTG TTDIGSNTTV KTGDLVTYDK ENGMHKKVFY SFIDDKNHNK     50
KLLVIRTKGT IAGQYRVYSE EGANKSGLAW PSAFKVQLQL PDNEVAQISD    100
YYPRNSIDTK EYMSTLTYGF NGNVTGDDTG KIGGLIGANV SIGHTLKYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTN          293
```

CITATION LIST

Patent Literature

[1] PCT/US2013/026514 (published as WO2013/123450) entitled "Methods for Creating Bilayers for Use with Nanopore Sensors"
[2] PCT/US2013/068967 (published as WO 2014/074727) entitled "Nucleic Acid Sequencing Using Tags"
[3] PCT/US14/61853 filed 23 Oct. 2014 entitled "Methods for Forming Lipid Bilayers on Biochips"

Non-Patent Literature

[4] Aksimentiev and Schulten, *Imaging a-Hemolysin with Molecular Dynamics: Ionic Conductance, Osmotic Permeability, and the Electrostatic Potential Map*, Biophysical Journal (2005) 88: 3745-3761.
[5] Butler et al., *Single-molecule DNA detection with an engineered MspA protein nanopore*, PNAS (2008) 105 (52): 20647-20652.
[6] Korchev et al., *Low Conductance States of a Single Ion Channel are not 'Closed'*, J. Membrane Biol. (1995) 147:233-239.
[7] Krasilnikov and Sabirov, *Ion Transport Through Channels Formed in Lipid Bilayers by Staphylococcus aureus Alpha-Toxin*, Gen. Physiol. Biophys. (1989) 8:213-222.
[8] Nakane et al., *A Nanosensor for Transmembrane Capture and Identification of Single Nucleic Acid Molecules*, Biophys. J. (2004) 87:615-621.
[9] Rhee and Burns, *Nanopore sequencing technology: nanopore preparations*, TRENDS in Biotech. (2007) 25(4):174-181.
[10] Song et al., Structure of *Staphylococcal α-Hemolysin, a Heptameric Transmembrane Pore*, Science (1996) 274: 1859-1866.
[11] Kasianowicz et al., *Nanometer-scale pores: potential applications for analyte detection and DNA characterization*, Proc. Natl. Acad. Sci. USA (1996) 93:13770-13773.
[12] Akeson et al., *Microsecond timescale discrimination among polycytidylic acid, polyadenylic acid, and polyuridylic acid as homopolymers or as segments within single RNA molecules*, Biophys. J. (1999) 77:3227-3233.
[13] Meller et al., *Voltage-driven DNA translocations through a nanopore*, Phys. Rev. Lett., 86 (2001), pp. 3435-3438.
[14] Howorka et al., *Sequence-specific detection of individual DNA strands using engineered nanopores*, Nat. Biotechnol., 19 (2001a), pp. 636-639.
[15] Howorka et al., *Kinetics of duplex formation for individual DNA strands within a single protein nanopore*, Proc. Natl. Acad. Sci. USA, 98 (2001b), pp. 12996-13001.
[16] Movileanu et al., *Detecting protein analytes that modulate transmembrane movement of a polymer chain within a single protein pore*, Nat. Biotechnol., 18 (2000), pp. 1091-1095.

The entirety of each patent, patent application, publication, document, GENBANK sequence, website and other published material referenced herein hereby is incorporated by reference, including all tables, drawings, and figures. All patents and publications are herein incorporated by reference to the same extent as if each was specifically and individually indicated to be incorporated by reference. Citation of the above patents, patent applications, publications and documents is not an admission that any of the foregoing is pertinent prior art, nor does it constitute any admission as to the contents or date of these publications or documents. All patents and publications mentioned herein are indicative of the skill levels of those of ordinary skill in the art to which the invention pertains.

---

What is claimed is:

1. An α-hemolysin (α-HL) variant comprising a substitution at a position corresponding to position 17 of SEQ ID NO:3, wherein the substitution is a positive charge substitution.

2. The α-hemolysin variant according to claim 1, wherein said variant further comprises H144A.

3. The α-hemolysin variant according to claim 1 or 2, wherein said variant comprises a substitution at positions corresponding to residue N17.

4. The α-hemolysin variant according to claim 1 or 2, wherein said variant comprises a substitution selected from N17K, N17R and combinations thereof.

5. The α-hemolysin (α-HL) variant according to claim 1, wherein the substitution is N17K.

6. The α-hemolysin (α-HL) variant according to claim 1, wherein the substitution is N17R.

7. The α-hemolysin (α-HL) variant according to claim 1, wherein the variant has a sequence having at least 80%, 90%, 95%, 98%, or more sequence identity to SEQ ID NO: 8.

8. An alpha-hemolysin variant according to claim 1 or 2, which is covalently bound to a DNA polymerase.

9. An alpha-hemolysin variant according to claim 8, wherein said variant is bound to the DNA polymerase via an isopeptide bond.

10. A heptameric nanopore assembly comprising at least one α-hemolysin (α-HL) variant according to any one of claim 1 or 2.

11. The heptameric nanopore assembly according to claim 10, wherein said pore assembly has an altered time to thread (TTT) relative to a pore complex consisting of native alpha-hemolysin.

12. The heptameric nanopore assembly according to claim 11, wherein the TTT is decreased.

13. A method for detecting a target molecule, comprising:
   (a) providing a chip comprising a nanopore according to claim 10 in a membrane that is disposed adjacent or in proximity to a sensing electrode;
   (b) directing a nucleic acid molecule through said nanopore, wherein said nucleic acid molecule is associated with a reporter molecule, wherein said nucleic acid molecule comprises an address region and a probe region, wherein said reporter molecule is associated with said nucleic acid molecule at said probe region, and wherein said reporter molecule is coupled to a target molecule;
   (c) sequencing said address region while said nucleic acid molecule is directed through said nanopore to determine a nucleic acid sequence of said address region; and
   (d) identifying, with the aid of a computer processor, said target molecule based upon a nucleic acid sequence of said address region determined in (c).

\* \* \* \* \*

SEQUENCE LISTING

```
<160> NUMBER OF SEQ ID NOS: 8

<210> SEQ ID NO 1
<211> LENGTH: 1023
<212> TYPE: DNA
<213> ORGANISM: Staphylococcus aureus

<400> SEQUENCE: 1
atggcagatc tcgatcccgc gaaattaata cgactcacta tagggaggcc acaacggttt      60
ccctctagaa ataattttgt ttaactttaa gaaggagata tacaaatgga ttcagatatt     120
aatattaaaa caggtacaac agatattggt tcaaatacaa cagtaaaaac tggtgattta     180
gtaacttatg ataagaaaa tggtatgcat aaaaaagtat tttattcttt tattgatgat     240
aaaaatcata ataaaaatt gttagttatt cgtacaaaag gtactattgc aggtcaatat     300
agagtatata gtgaagaagg tgctaataaa agtggtttag catggccatc tgctttaaa      360 gttcaattac aattacctga taatgaagta gcacaaattt cagattatta tccacgtaat     420
agtattgata caaaagaata tatgtcaaca ttaacttatg gttttaatgg taatgtaaca     480
ggtgatgata ctggtaaaat tggtggttta attggtgcta atgtttcaat tggtcataca     540
ttaaaatatg tacaaccaga ttttaaaaca attttagaaa gtcctactga taaaaaagtt     600
ggttggaaag taatttttaa taatatggtt aatcaaaatt ggggtcctta tgatcgtgat     660
agttggaatc ctgtatatgg taatcaatta tttatgaaaa caagaaatgg ttctatgaaa     720
```

```
gcagctgata atttcttaga tccaaataaa gcatcaagtt tattatcttc aggtttttct    780
cctgattttg caacagttat tactatggat agaaaagcat caaaacaaca aacaaatatt    840
gatgttattt atgaacgtgt aagagatgat tatcaattac attggacatc aactaattgg    900
aaaggtacaa atactaaaga taatggaca gatagaagtt cagaaagata taaaattgat     960
tgggaaaaag aagaaatgac aaatggtctc agcgcttgga gccacccgca gttcgaaaaa   1020
taa                                                                 1023
```

<210> SEQ ID NO 2
<211> LENGTH: 306
<212> TYPE: PRT
<213> ORGANISM: Staphylococcus aureus

<400> SEQUENCE: 2

```
Met Ala Asp Ser Asp Ile Asn Ile Lys Thr Gly Thr Thr Asp Ile Gly
 1               5                  10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

Gln Tyr Arg Val Tyr Ser Glu Glu Gly Ala Asn Lys Ser Gly Leu Ala
65                  70                  75                  80

Trp Pro Ser Ala Phe Lys Val Gln Leu Gln Leu Pro Asp Asn Glu Val
                85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Gly Asn Val Thr Gly Asp
        115                 120                 125

Asp Thr Gly Lys Ile Gly Gly Leu Ile Gly Ala Asn Val Ser Ile Gly
    130                 135                 140

His Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205

Asp Asn Phe Leu Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
                245                 250                 255

Tyr Gln Leu His Trp Thr Ser Thr Asn Trp Lys Gly Thr Asn Thr Lys
            260                 265                 270

Asp Lys Trp Thr Asp Arg Ser Glu Arg Tyr Lys Ile Asp Trp Glu
        275                 280                 285

Lys Glu Glu Met Thr Asn Gly Leu Ser Ala Trp Ser His Pro Gln Phe
    290                 295                 300

Glu Lys
305
```

<210> SEQ ID NO 3
<211> LENGTH: 305
<212> TYPE: PRT
<213> ORGANISM: Staphylococcus aureus

<400> SEQUENCE: 3

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Gly Leu Ser Ala Trp Ser His Pro Gln Phe Glu
    290                 295                 300

Lys
305
```

<210> SEQ ID NO 4
<211> LENGTH: 305
<212> TYPE: PRT
<213> ORGANISM: Staphylococcus aureus

<400> SEQUENCE: 4

```
Ala Asp Ser Asp Ile Asn Ile Lys Thr Gly Thr Thr Asp Ile Gly Ser
1               5                   10                  15
```

```
Lys Thr Thr Val Lys Thr Gly Asp Leu Val Thr Tyr Asp Lys Glu Asn
             20                  25                  30

Gly Met His Lys Lys Val Phe Tyr Ser Phe Ile Asp Asp Lys Asn His
             35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
                100                 105                 110

Met Ser Thr Leu Thr Tyr Gly Phe Asn Gly Asn Val Thr Gly Asp Asp
                115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
                195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Thr Asp Arg Ser Ser Glu Arg Tyr Lys Ile Asp Trp Glu Lys
                275                 280                 285

Glu Glu Met Thr Asn Gly Leu Ser Ala Trp Ser His Pro Gln Phe Glu
                290                 295                 300

Lys
305

<210> SEQ ID NO 5
<211> LENGTH: 305
<212> TYPE: PRT
<213> ORGANISM: Staphylococcus aureus

<400> SEQUENCE: 5

Ala Asp Ser Asp Ile Asn Ile Lys Thr Gly Thr Thr Asp Ile Gly Ser
 1               5                  10                  15

Arg Thr Thr Val Lys Thr Gly Asp Leu Val Thr Tyr Asp Lys Glu Asn
             20                  25                  30

Gly Met His Lys Lys Val Phe Tyr Ser Phe Ile Asp Asp Lys Asn His
             35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
```

```
                65                  70                  75                  80
        Pro Ser Ala Phe Lys Val Gln Leu Gln Leu Pro Asp Asn Glu Val Ala
                        85                  90                  95

Gln Ile Ser Asp Tyr Tyr Pro Arg Asn Ser Ile Asp Thr Lys Glu Tyr
                        100                 105                 110

Met Ser Thr Leu Thr Tyr Gly Phe Asn Gly Asn Val Thr Gly Asp Asp
                        115                 120                 125

Thr Gly Lys Ile Gly Gly Leu Ile Gly Ala Asn Val Ser Ile Gly His
                    130                 135                 140

Thr Leu Lys Tyr Val Gln Pro Asp Phe Lys Thr Ile Leu Glu Ser Pro
        145                 150                 155                 160

Thr Asp Lys Lys Val Gly Trp Lys Val Ile Phe Asn Asn Met Val Asn
                        165                 170                 175

Gln Asn Trp Gly Pro Tyr Asp Arg Asp Ser Trp Asn Pro Val Tyr Gly
                        180                 185                 190

Asn Gln Leu Phe Met Lys Thr Arg Asn Gly Ser Met Lys Ala Ala Asp
                    195                 200                 205

Asn Phe Leu Asp Pro Asn Lys Ala Ser Ser Leu Leu Ser Ser Gly Phe
                210                 215                 220

Ser Pro Asp Phe Ala Thr Val Ile Thr Met Asp Arg Lys Ala Ser Lys
        225                 230                 235                 240

Gln Gln Thr Asn Ile Asp Val Ile Tyr Glu Arg Val Arg Asp Asp Tyr
                        245                 250                 255

Gln Leu His Trp Thr Ser Thr Asn Trp Lys Gly Thr Asn Thr Lys Asp
                    260                 265                 270

Lys Trp Thr Asp Arg Ser Ser Glu Arg Tyr Lys Ile Asp Trp Glu Lys
                275                 280                 285

Glu Glu Met Thr Asn Gly Leu Ser Ala Trp Ser His Pro Gln Phe Glu
                    290                 295                 300

Lys
        305

<210> SEQ ID NO 6
<211> LENGTH: 305
<212> TYPE: PRT
<213> ORGANISM: Staphylococcus aureus

<400> SEQUENCE: 6

Ala Asp Ser Asp Ile Asn Ile Lys Thr Gly Thr Lys Asp Ile Gly Ser
        1               5                   10                  15

Asn Thr Thr Val Lys Thr Gly Asp Leu Val Thr Tyr Asp Lys Glu Asn
                        20                  25                  30

Gly Met His Lys Lys Val Phe Tyr Ser Phe Ile Asp Asp Lys Asn His
                    35                  40                  45

Asn Lys Lys Leu Leu Val Ile Arg Thr Lys Gly Thr Ile Ala Gly Gln
                50                  55                  60

Tyr Arg Val Tyr Ser Glu Gly Ala Asn Lys Ser Gly Leu Ala Trp
        65                  70                  75                  80

Pro Ser Ala Phe Lys Val Gln Leu Gln Leu Pro Asp Asn Glu Val Ala
                        85                  90                  95

Gln Ile Ser Asp Tyr Tyr Pro Arg Asn Ser Ile Asp Thr Lys Glu Tyr
                        100                 105                 110

Met Ser Thr Leu Thr Tyr Gly Phe Asn Gly Asn Val Thr Gly Asp Asp
                        115                 120                 125
```

```
Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
            275                 280                 285

Glu Glu Met Thr Asn Gly Leu Ser Ala Trp Ser His Pro Gln Phe Glu
            290                 295                 300

Lys
305

<210> SEQ ID NO 7
<211> LENGTH: 305
<212> TYPE: PRT
<213> ORGANISM: Staphylococcus aureus

<400> SEQUENCE: 7

Ala Asp Ser Asp Ile Asn Ile Lys Thr Gly Thr Arg Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190
```

```
Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
            275                 280                 285

Glu Glu Met Thr Asn Gly Leu Ser Ala Trp Ser His Pro Gln Phe Glu
            290                 295                 300

Lys
305

<210> SEQ ID NO 8
<211> LENGTH: 293
<212> TYPE: PRT
<213> ORGANISM: Staphylococcus aureus

<400> SEQUENCE: 8

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
            85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
            165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
```

```
                    245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```